Figure 12:
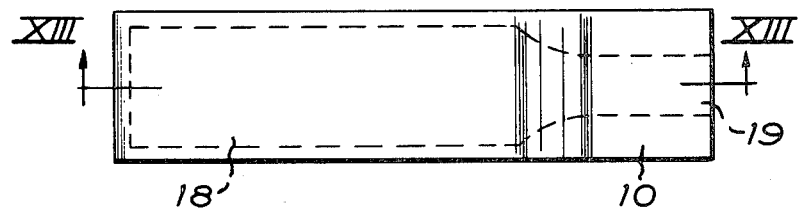

United States Patent [19]

Lilja et al.

[11] 4,088,448

[45] May 9, 1978

[54] APPARATUS FOR SAMPLING, MIXING THE SAMPLE WITH A REAGENT AND MAKING PARTICULARLY OPTICAL ANALYSES

[76] Inventors: Jan Evert Lilja, Frodes vag 17, 291 65 Kristianstad; Sven Erik Lennart Nilsson, Hasselvagen 17, Kristianstad, both of Sweden

[21] Appl. No.: 724,054

[22] Filed: Sep. 16, 1976

[30] Foreign Application Priority Data

Sep. 29, 1975 Sweden .................... 7510863

[51] Int. Cl.² ................ G01N 33/16; G01N 21/24
[52] U.S. Cl. ................ 23/259; 23/230 B; 23/253 TP; 23/253 R; 128/2 F; 356/246
[58] Field of Search ............... 23/253 R, 259, 253 TP, 23/230 B; 356/246; 128/2 F

[56] References Cited

U.S. PATENT DOCUMENTS

| | | | |
|---|---|---|---|
| 3,464,800 | 9/1969 | Gerade | 23/259 |
| 3,497,320 | 2/1970 | Blackburn et al. | 23/253 R |
| 3,582,285 | 6/1971 | Hamilton | 356/246 X |
| 3,620,676 | 11/1971 | Davis | 23/253 TP |
| 3,640,267 | 2/1972 | Hurtig et al. | 128/2 F |
| 3,690,836 | 9/1972 | Buissiere et al. | 23/253 TP |
| 3,701,633 | 10/1972 | Davis | 23/253 TP |
| 3,732,079 | 5/1973 | Davis | 23/253 TP |
| 3,768,978 | 10/1973 | Grubb et al. | 123/2 F |
| 3,770,382 | 11/1973 | Carter et al. | 356/246 X |
| 3,799,742 | 3/1974 | Coleman | 356/246 X |
| 3,811,840 | 5/1974 | Bauer et al. | 23/253 TP |
| 3,838,013 | 9/1974 | Bergeron | 195/139 |
| 3,859,050 | 1/1975 | Hern et al. | 23/253 R |
| 3,860,347 | 1/1975 | Jones | 356/246 |
| 3,951,606 | 4/1976 | Moyer et al. | 23/259 X |
| 3,994,594 | 11/1976 | Sandrock et al. | 356/246 |

FOREIGN PATENT DOCUMENTS

| | | |
|---|---|---|
| 2,103,841 | 10/1972 | Germany. |
| 2,422,260 | 11/1975 | Germany. |
| 1,307,704 | 2/1973 | United Kingdom. |
| 1,353,632 | 5/1974 | United Kingdom. |

OTHER PUBLICATIONS

Bowman et al., "Capillary-Tube Scanner for Mechanized Microbiology", Science, vol. 158, 1967, pp. 78-83.

*Primary Examiner*—R.E. Serwin
*Attorney, Agent, or Firm*—Beveridge, DeGrandi, Kline & Lunsford

[57] ABSTRACT

A cuvette for sampling with a cavity which is defined by two planar surfaces which are placed or can be placed at a predetermined distance from one another. A reagent is contained in the cavity in an amount which is exactly determined in relation to the volume of the cavity. The sample is drawn into the cavity preferably by capillary force and mixed with the reagent therein spontaneously or by vibration, whereupon optical analysis takes place directly through the two planar surfaces.

16 Claims, 15 Drawing Figures

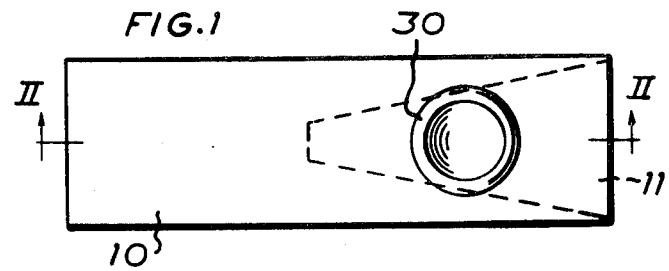
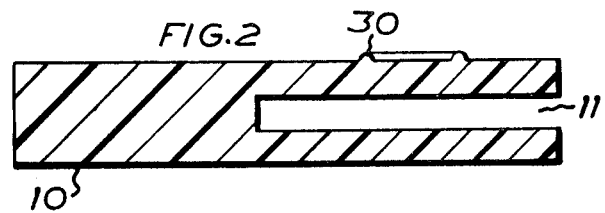
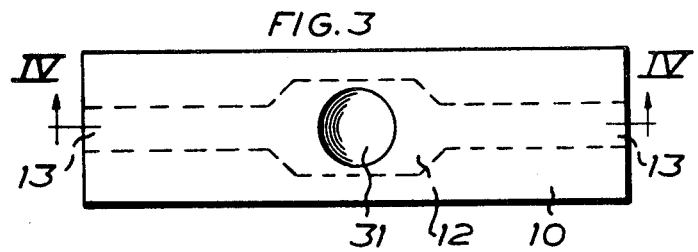
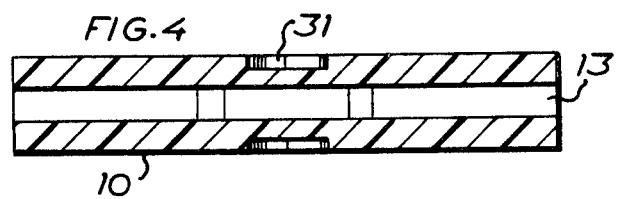
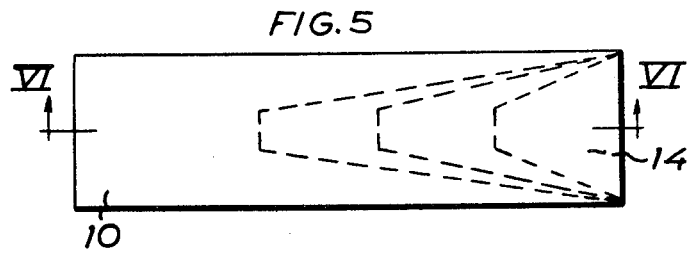
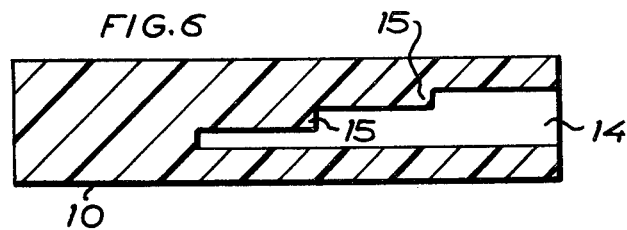

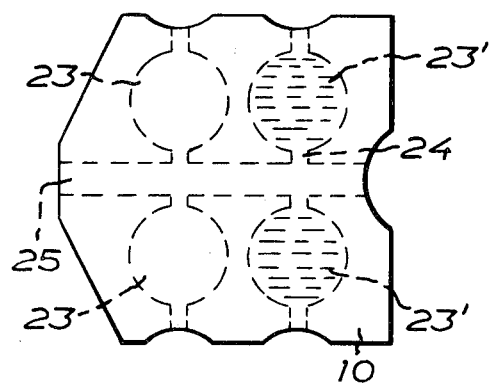
FIG.7
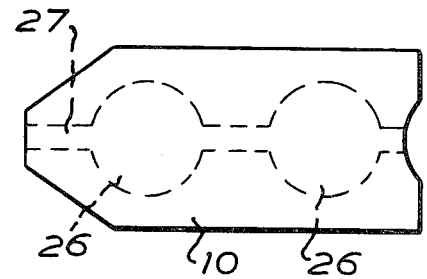
FIG.8
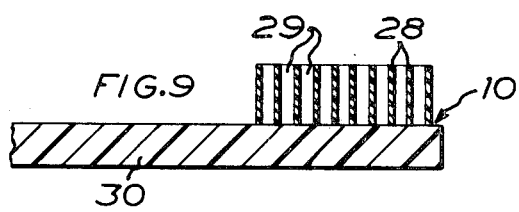
FIG.9
FIG.11
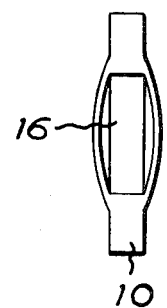
FIG.10
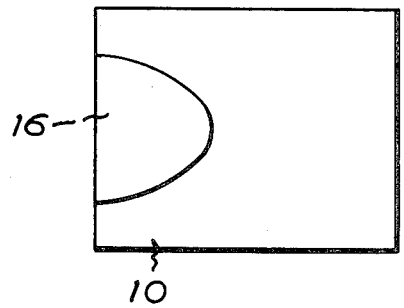

APPARATUS FOR SAMPLING, MIXING THE SAMPLE WITH A REAGENT AND MAKING PARTICULARLY OPTICAL ANALYSES

This invention relates to an apparatus for sampling, mixing the sample with a reagent and directly making particularly optical analyses of the sample mixed with the reagent.

In making wet-chemical analyses a sample is normally measured with a single-use pipette while the reagent is measured in a vessel with a pipette or dispensor. The reagent mostly has a relatively large volume, which results in a relatively small error on measuring the volume, whereas the volume of the sample normally is small, which implies a high dilution after mixing of reagent and sample. To attain a high precision the sample volume must therefore be measured with great exactitude. The sample and reagent mixture is transferred after the reaction time, if any, to an optical measuring cuvette for measurement.

The object of the present invention is to overcome the disadvantages prevailing in analyses of this kind.

To this end there is provided a measuring cuvette which is characterized in that it comprises a body having at least one cavity into which the sample can be drawn, in that the reagent is accommodated in the cavity in an amount predetermined in relation to the volume of said cavity, and in that two opposed planar surfaces defining the cavity are placed or adapted to be placed at a predetermined distance from each other.

The invention permits sampling of a liquid, mixing and chemically reacting it with a suitable reagent, for instance for colour development, in the same vessel as the one used for the subsequent measurement. The invention thus simplifies the sampling procedure, reduces the number of utensils and in most cases, depending upon the type of analysis, considerably improves the exactitude of the analysis by making the analysing procedure independent of the operating technique of the operator making the analysis. Compared with the conventional manual procedures, the gain of time is also considerable.

According to the invention the cuvette may be in the form of an optical measuring cuvette of short light path, which is primarily intended for directly sucking up a sample by the capillary force arising between the walls defining the cavity of the cuvette, by vacuum or by gravity. The cuvette cavity contains an exactly determined amount of reagent, preferably in solid form. The remaining volume of the cuvette cavity is filled with sample liquid. This gives a definite volume relation of the sample liquid to the reagent. The sample liquid is meant to dissolve the reagent, which implies that two earlier manual measuring procedures are replaced by one in which the manufacturing exactitude will be determinative of the measuring exactitude.

The reagent recipe is so formulated that the dissolution of the reagent does not take place too rapidly. An increased dissolution rate is obtained by means of vibratory mixing. The dissolution rate can also be influenced if the reagent is coated with a suitable difficulty soluble substance, which in turn entails the possibility of carrying out chemical reactions in several steps and of separating sensitive reagents.

Mixing suitably takes place by vibration since the liquid layer is so thin that the conventional mixing procedures are ineffective. Mixing is most simply carried out in a photometer but can also be carried out in a separate vibrator. The optimum vibration frequency and amplitude to a certain extent are dependent upon the physical configuration and location of the measuring cuvette. If use is made of a separate vibrator a standard photometer can be utilized on making optical analyses.

Figure 13:
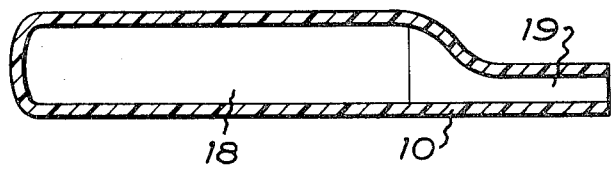
Figure 14:
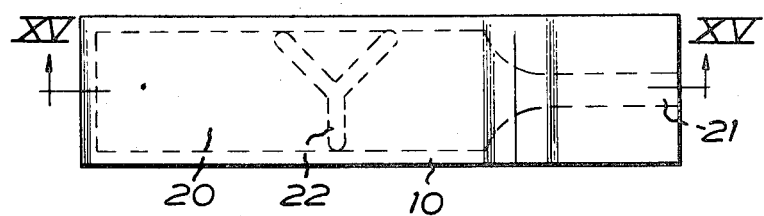
Figure 15:
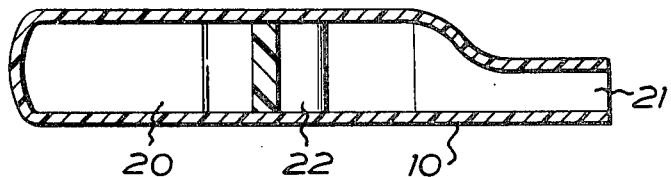

The invention shall be described more in detail in the following with reference to the accompanying drawings which schematically and on a large scale illustrate several embodiments. In the drawings:

FIG. 1 shows a measuring cuvette according to the invention;
FIG. 2 shows a section on the line II—II in FIG. 1;
FIG. 3 shows a modified embodiment of the cuvette;
FIG. 4 shows a section on the line IV—IV in FIG. 3;
FIG. 5 shows another embodiment of the measuring cuvette according to the invention;
FIG. 6 shows a section on the line VI—VI in FIG. 5;
FIG. 7 shows an embodiment in which the cuvette has parallel-connected cavities;
FIG. 8 shows an embodiment in which the cuvette has series-connected cavities;
FIG. 9 shows a further embodiment in which the cuvette has a plurality of cavities in the form of channels;
FIG. 10 shows a cuvette with somewhat outwardly bulging walls;
FIG. 11 shows the cuvette according to FIG. 10 from one end;
FIG. 12 shows a cuvette having an inlet channel;
FIG. 13 shows this cuvette in section on the line XIII—XIII;
FIG. 14 shows a cuvette having a spacing element; and
FIG. 15 shows a section on the line XV—XV in FIG. 14.

The cuvette illustrated in the drawings comprises a body 10 of glass or plastics which is preferably transparent to permit making optical analyses. According to FIGS. 1 and 2 the body 10 has a cavity 11 which is intended to accommodate a liquid sample and the dimension of which is such that it can be filled by capillary force or, in some cases, by gravity. The dimensions of the cavity are exactly determined, in particular the distance between the walls defining the cavity.

The cavity 11 of the cuvette is supplied with a reagent (that is, an agent to react with the sample drawn into said cavity) by evaporation, freeze-drying, spraying, screen printing or in another suitable manner according to the manner in which the cuvette is manufactured. The amount of reagent is thoroughly regulated in dependence on the size of the cavity. By coating the reagent the dissolution rate thereof in the sample can be controlled, for instance for the dissolution of reagents in a definite sequence, which is suitable in making analyses in several reaction steps, or for the isolation of sensitive reagents. After a reagent has been deposited in the cavity the cuvette is ready for use. When the cuvette illustrated in FIG. 1 is to be used the outwardly open side of the cavity is brought in contact with the liquid sample to be examined, whereby said sample penetrates into the cavity 10 and there mixes with the reagent either spontaneously or with the aid of, for instance, a vibrator which may be a separate unit or part of the analysing apparatus, for instance a photometer, in which the sample is to be analysed. The sample is then placed in the analysing apparatus, and the analysis is carried out.

As will appear from FIGS. 1 and 2 an annular bead 30 is disposed on the outer side of the upper wall defining the cavity (see FIG. 2). This bead 30 has for its object to protect the enclosed portion of the wall against being scratched or otherwise damaged when the cuvette is handled before making the analysis.

FIGS. 3 and 4 show a modified embodiment of the cuvette 10 which has a cavity 12 and two channels 13 which extend from opposite sides of the cuvette and open into the cavity 12. Thus a sample can here be drawn straight through the cuvette, which may be advantageous in certain cases. A recess 31 having a planar bottom is arranged in each of the opposite walls of the cuvette above the cavity 12. Said recesses are situated opposite one another and serve the same purpose as the annular bead 30 in the foregoing embodiment.

The cuvette according to FIGS. 5 and 6 has a cavity 14 of varying depth, which has been realized by stepping one of the surfaces of the cavity to form levels 15 spaced different distances from the opposite surface. The number of such levels can be varied and the height difference between the levels will be determinative for the measuring exactitude. The outermost cavity can serve as a receiving cavity which is devoid of reagent and from which the sample can be drawn at a suitable rate into the other cavities. Of course, a bead 30 or recess 31 according to the two preceding embodiments may be disposed above one or more levels.

The cuvette as shown in FIG. 7 has four parallel-connected cavities 23, 23', which are linked to a common channel 25 by branch channels 24 which continue on the opposite side of the cavities and open into the atmosphere to prevent air inclusions in the cavities when samples are drawn thereinto. The cavities 23, 23' can contain reagents of the same or different kinds for making control analyses and various kinds of analyses, respectively. In a preferred embodiment the cavities 23' instead of containing a reagent deposited on the walls thereof, may contain a gel, for instance, one gel of a given type in the upper cavity of the figure and another gel in the lower cavity thereof. This will provide the advantage that a sample can be caused to react with two different reagents in the cavities 23 while particles of a size determined by the choice of gel diffuses into the gel in the respective cavity 23' to react with a specific reagent contained in the gel.

FIG. 8 shows two series-connected cuvette cavities 26 into which a sample is drawn through a channel 27. Said cavities may contain reagents of the same kind for making control analyses or of different kinds for making different analyses. As in the previous embodiment one cavity may contain a reagent and the other cavity — the inner one — a gel.

The embodiment according to FIG. 9 differs from those already described in that the cuvette is formed by a supporting plate 30 on which is fixed, for instance by gluing, a rigid porous material 28 with channels or cavities 29 extending at right angles to the plane of the supporting plate. Same as in the preceding embodiments, a reagent cr reagents are deposited in said channels or cavities 29. In this case the distance between the end surfaces of the channels or cavities is of importance as the analysis here takes place in the longitudinal direction of the channels or cavities. Of course, like in the preceding examples, the channel volume is of importance.

The cuvette shown in FIGS. 10 and 11 is made of a more elastic plastic material than the preceding cuvettes and has a cavity 16 which — as will appear from the end view in FIG. 11 — is defined by outwardly bulging walls which by a mechanical device are compressed to take a predetermined distance from each other at the subsequent analysis. The cuvette according to FIGS. 12 and 13 likewise consists of elastic plastic material and has a cavity 18 with an inlet channel 19. In this case also the walls defining the cavity are compressed at the subsequent analysis. The thickness tolerance of the cuvette material will be decisive of the measuring exactitude both in the former and the latter apparatus, as will the stability of the device by means of which the walls are compressed.

The cuvette shown in FIGS. 14 and 15 is also made of elastic material and formed with a cavity 20 and inlet channel 21 in the same way as the cuvette shown in FIG. 12. But the cuvette in FIGS. 14 and 15 has an internal spacing element 22 which can serve to determine the interstice to which the surfaces defining the cavity 20 can be compressed, and to support the reagent. Besides, the spacing element 22 may have a mixing function if it is made of ferromagnetic material and mixing is realized by placing the cuvette in a variable magnetic field.

The cuvettes illustrated in FIGS. 10-15 can be filled by capillary force, gravity or vacuum.

In case the sample drawn into the cuvette shall not be immediately analysed or in case the analysis takes a long time, means may be provided to close the outwardly facing open end of the cavity and inlet channel, respectively. Such means may be a plastic hood which is pulled over the opening, or a material of suitable consistency into which the cuvette is dipped and which immediately seals the opening.

If desired, the cuvette can readily be provided with means such as projections and recesses which operate measuring equipment at the subsequent analysis.

The measuring cuvette described is useful for making analyses of the most varying kinds. It has, however, been found to be of special advantage in the determination of hemoglobin, where it has proved possible to reduce the error margin to an absolute minimum. If the cuvette has a receiving cavity into which the sample is drawn by vacuum, gravity or capillary force and from which the sample is supplied, by capillary force, to a plurality of cavities containing different reagents and-/or gels a large number of analyses can be rapidly made particularly if the cuvette is fed into an automatic measuring apparatus which is controlled by specially designed cuvette parts.

As will appear from the foregoing, the cuvette according to the invention in an extremely simple way permits making analyses which without exception have hitherto been difficult and time-consuming and necessitated great skill of the operator to avoid errors.

What we claim and desire to secure by Letters Patent is:

1. A cuvette for sampling a fluid, mixing the sample with a reagent, and directly making optical analyses of the sample mixed with the reagent, comprising a body member including two planar surfaces defining an optical path and placed at a predetermined distance from one another to determine the optical path length and to define at least one cavity having an inlet communicating the at least one cavity with the exterior of the body member, the at least one cavity having a predetermined fixed volume, the predetermined distance being effective to permit the sample to enter the cavity by capillary force; and a reagent coated on the cavity surface.

2. A cuvette as claimed in claim 1, wherein the reagent is in the form of a solid material deposited on the walls of the cavity by evaporation, freeze-drying, spraying or screen printing.

3. A cuvette as claimed in claim 1, wherein the reagent is in the form of a semi-solid material, particularly a gel.

4. A cuvette as claimed in claim 1, wherein the cuvette has a receiving space communicating with the at least one cavity and with the inlet and from which the at least one cavity withdraws the sample by capillary force.

5. A cuvette as claimed in claim 1, wherein said body member has a plurality of cavities arranged in parallel or in series, said cavities containing the same or different reagents.

6. A cuvette as claimed in claim 1, wherein said body member is adapted for mixing of the sample with the reagent by actuation from the outer side of the body member.

7. A cuvette as claimed in claim 6, wherein said body member is adapted for mixing actuation by vibration.

8. A cuvette as claimed in claim 1, wherein at least one of the walls defining the cavity of the body member is stepped with exactly determined height differences between the different steps.

9. A cuvette as claimed in claim 1, wherein the reagent or reagents are coated for regulation of the dissolution rate.

10. A cuvette as claimed in claim 1, wherein the at least one cavity is oriented with its longitudinal direction at right angles with the body member planar surfaces.

11. A cuvette as claimed in claim 1, made from transparent plastic material or glass.

12. A cuvette for sampling a fluid, mixing the sample with a reagent, and directly making optical analyses of the sample mixed with the reagent, comprising a body member including two flexible surfaces and means joining the two surfaces to define at least one cavity having an inlet communicating the at least one cavity with the exterior of the body member, the joining means separating the flexible surfaces by a dimension effective to permit the sample to enter the at least one cavity by capillary force, the two flexible surfaces being adapted to be placed at a predetermined distance from one another by actuation from the outer side of the body member to define an optical path having a predetermined optical path length and to provide a predetermined volume in the cavity; and a reagent coated on the cavity surface.

13. A cuvette as claimed in claim 12, further comprising a spacing element disposed in the cavity to determine the distance between the walls of the cavity upon actuation of said walls from outside.

14. A cuvette as claimed in claim 13, wherein the reagent is carried by the spacing element.

15. A cuvette as claimed in claim 13, wherein the spacing element is of ferromagnetic material to provide mixing of the sample and the reagent when the cuvette is placed in a variable magnetic field.

16. A cuvette as claimed in claim 12 further comprising a reagent in the cavity in the predetermined amount.

* * * * *